United States Patent
Taglione et al.

(10) Patent No.: US 9,541,529 B2
(45) Date of Patent: Jan. 10, 2017

(54) ULTRASONIC PROBE FOR EXAMINING AN OBJECT WITH ULTRASOUND AND CORRESPONDING EXAMINATION METHOD

(71) Applicant: AREVA NP, Courbevoie (FR)

(72) Inventors: Matthieu Taglione, Dijon (FR); Yannick Caulier, Chalon sur Saone (FR)

(73) Assignee: AREVA NP, Courbevoie (FR)

( * ) Notice: Subject to any disclaimer, the term of this patent is extended or adjusted under 35 U.S.C. 154(b) by 281 days.

(21) Appl. No.: 14/509,455

(22) Filed: Oct. 8, 2014

(65) Prior Publication Data

US 2015/0096381 A1 Apr. 9, 2015

(30) Foreign Application Priority Data

Oct. 9, 2013 (FR) .................................... 13 59807

(51) Int. Cl.
 *G01B 17/02* (2006.01)
 *G01N 29/24* (2006.01)
 (Continued)

(52) U.S. Cl.
 CPC ........... *G01N 29/2418* (2013.01); *G01B 11/24* (2013.01); *G01B 17/06* (2013.01);
 (Continued)

(58) Field of Classification Search
 CPC ................... G01N 29/2418; G01N 2291/028; G01N 29/262; G01N 21/8803; G01B 21/20; G01B 17/06
 See application file for complete search history.

(56) References Cited

U.S. PATENT DOCUMENTS

| 3,804,521 A | * | 4/1974 | Sprague | ................. G02B 27/48 356/446 |
| 4,334,780 A | * | 6/1982 | Pernick | ................. G01B 11/303 356/446 |

(Continued)

FOREIGN PATENT DOCUMENTS

| FR | | 2930642 A1 | 10/2009 | |
| FR | | EP 2860522 A1 * | 4/2015 | ........... G01N 29/262 |
| WO | WO 2005/050617 A2 | | 6/2005 | |

OTHER PUBLICATIONS

European Search Report for EP 2860522 A1.*

*Primary Examiner* — Harshad R Patel
*Assistant Examiner* — Samir M Shah
(74) *Attorney, Agent, or Firm* — Davidson, Davidson & Kappel, LLC

(57) ABSTRACT

An ultrasonic probe for examining an object with ultrasound and a corresponding examination method are provided. The probe includes a plurality of emitter elements able to emit ultrasonic waves for emitting a focused ultrasonic beam into the object through an active area of a surface of the object, and a profilometer for determining the profile of the surface of the object and for controlling the emission of the ultrasonic beam depending on the determined profile. The profilometer includes an image-taking apparatus for taking at least one digital image of the active area and an image processing module able to determine the profile of the active area by analyzing the optical blurring of the or at least one image.

10 Claims, 3 Drawing Sheets

(51) Int. Cl.
*G01B 21/20* (2006.01)
*G01N 29/26* (2006.01)
*G01N 21/88* (2006.01)
*G01B 17/06* (2006.01)
*G01B 11/24* (2006.01)

(52) U.S. Cl.
CPC ......... *G01B 21/20* (2013.01); *G01N 21/8803* (2013.01); *G01N 29/262* (2013.01); *G01N 2291/028* (2013.01); *G01N 2291/106* (2013.01)

(56) References Cited

U.S. PATENT DOCUMENTS

| | | | | |
|---|---|---|---|---|
| 4,437,468 A * | 3/1984 | Sorenson | ............ | A61B 8/0875 600/459 |
| 4,824,250 A * | 4/1989 | Newman | ................ | G01N 21/88 356/502 |
| 5,485,263 A * | 1/1996 | Bjorner | ................ | G06K 7/10811 356/4.01 |
| 5,585,921 A * | 12/1996 | Pepper | ................ | G01N 29/075 356/432 |
| 5,680,863 A * | 10/1997 | Hossack | ................ | A61B 8/12 600/437 |
| 5,748,311 A * | 5/1998 | Hamann | ............ | G01N 15/0205 250/574 |
| 5,913,825 A * | 6/1999 | Watanabe | ............ | A61B 8/4281 600/459 |
| 6,208,749 B1 * | 3/2001 | Gutkowicz-Krusin | | A61B 5/442 356/303 |
| 6,424,597 B1 * | 7/2002 | Bolomey | ............ | G01N 29/262 367/128 |
| 7,123,363 B2 * | 10/2006 | Puttappa | ............ | A61B 5/14532 356/450 |
| 7,955,266 B2 * | 6/2011 | Casula | ................ | G10K 11/346 310/334 |
| 8,270,254 B2 * | 9/2012 | Casula | ................ | G01N 29/041 367/138 |
| 9,013,706 B2 * | 4/2015 | Yen | ........................ | G01N 21/55 356/450 |
| 2002/0183601 A1 * | 12/2002 | Tearney | ............. | A61B 1/00082 600/310 |
| 2004/0152989 A1 * | 8/2004 | Puttappa | ............ | A61B 5/14532 600/473 |
| 2007/0034010 A1 * | 2/2007 | Langlois | ............ | G01N 29/0609 73/584 |
| 2007/0167800 A1 * | 7/2007 | Casula | ................ | G10K 11/346 600/459 |
| 2008/0123106 A1 * | 5/2008 | Zeng | .................... | A61B 5/0066 356/600 |
| 2011/0032800 A1 * | 2/2011 | Casula | ................ | G01N 29/041 367/120 |
| 2013/0047729 A1 * | 2/2013 | Wigh | ................ | G01N 29/043 73/636 |
| 2014/0036042 A1 * | 2/2014 | Xia | ...................... | G02B 21/361 348/49 |

* cited by examiner

ULTRASONIC PROBE FOR EXAMINING AN OBJECT WITH ULTRASOUND AND CORRESPONDING EXAMINATION METHOD

The present invention relates to an ultrasonic probe with multiple ultrasonic emitter elements, for examining an object with ultrasound.

Such an ultrasonic probe gives the possibility of carrying out non-destructive examinations of an object. Such an ultrasonic probe may be used for examining surfaces and walls of a nuclear reactor, notably for examining welds of these walls (walls of a steam generator or of other components, such as J-shaped welds for example).

An ultrasonic probe with multiple ultrasonic emitter elements allows emission of a focused ultrasonic beam into the examined object. The ultrasonic beam corresponds to the sum of elementary ultrasonic signals emitted by the ultrasonic emitter elements. The focusing of the beam is obtained by controlling the ultrasonic emitter elements by means of delay laws for focusing the ultrasonic energy in different points of interest of the examined object by space-time synchronization. The delay laws give the possibility of emitting elementary ultrasonic signals with time delays as so that the elementary ultrasonic signal arrives in phase at the point of interest.

BACKGROUND

Ultrasonic probes are known from WO2005/050617, US 2013/047729 A1 and FR2930642.

In the case of an object comprising a non-planar or rough surface, it is necessary to correct the delay laws depending on the profile of the surface. To do this, it is possible to provide the ultrasonic probe with a profilometer able to determine the profile of the surface for correcting the delay laws depending on the determined profile, as in WO2005/050617.

SUMMARY OF THE INVENTION

One of the objects of the invention is to propose an ultrasonic probe which is simple and easy to apply.

For this purpose, an ultrasonic probe is provided for examining an object with ultrasound, the probe comprising a plurality of emitter elements capable of emitting ultrasonic waves so as to emit a focused ultrasonic beam in the object through an active area of a surface of the object, a profilometer for determining the profile of the surface of the object and controlling the emission of the ultrasonic beam depending on the determined profile, wherein the profilometer comprises an image-taking apparatus in order to at least take one digital image of the active area and an image processing module capable of determining the profile of the active area by analyzing the optical blurring of the or at least one image.

According to particular embodiments, the ultrasonic probe comprises one or several of the following features, taken individually or according to all the technically possible combinations:

the profilometer is able to take several images of the active area by moving a focal plane of the image-taking apparatus relatively to the active area between the taking of images;

the image-taking apparatus is movably mounted on a body of the ultrasonic probe so as to be able to move the focal plane of image-taking apparatus relatively to the active area between the taking of images;

the image-taking apparatus has an optical objective which is adjustable so as to be able to move the focal plane of the image-taking apparatus relatively to the active area between the taking of images;

the image-taking apparatus is positioned so as to take images of the active area through an emitting surface on which are distributed the emitter elements, when the ultrasonic probe is applied against the object to be examined;

the ultrasonic probe is configured so that an emitting surface of the probe on which are distributed the emitter elements, is outside of the field of vision of the image-taking apparatus, when the probe is applied against the object to be examined;

the ultrasonic probe is configured so that the image-taking apparatus takes pictures of the active area with a non-zero angle between the optical axis of the image-taking apparatus and the normal to the active area, when the probe is applied against the object to be examined;

the image-taking apparatus is positioned for taking images of a downstream area of the surface of the object located upstream from the active area during the movement of the probe along the surface of the object.

A method for non-destructive examination of an object having a surface is also provided, the method comprising:

the determination of a profile of an active area of the surface by taking at least one digital image of the active area and by analyzing the optical blurring of the or at least one image by means of a profilometer;

the emission of a focused ultrasonic beam into the object through the active area by means of a plurality of ultrasonic emitter elements, each ultrasonic emitter element being controlled depending on the determined profile.

In an embodiment, several images of the active area are taken by means of an image-taking apparatus of the profilometer by modifying the relative position of the active area and of the focal plane of the image-taking apparatus between each taking of an image.

BRIEF SUMMARY OF THE DRAWINGS

The invention and the advantages thereof will be better understood upon reading the description which follows, only given as an example and made with reference to the appended drawings, wherein.

DETAILED DESCRIPTION

Figure 1:
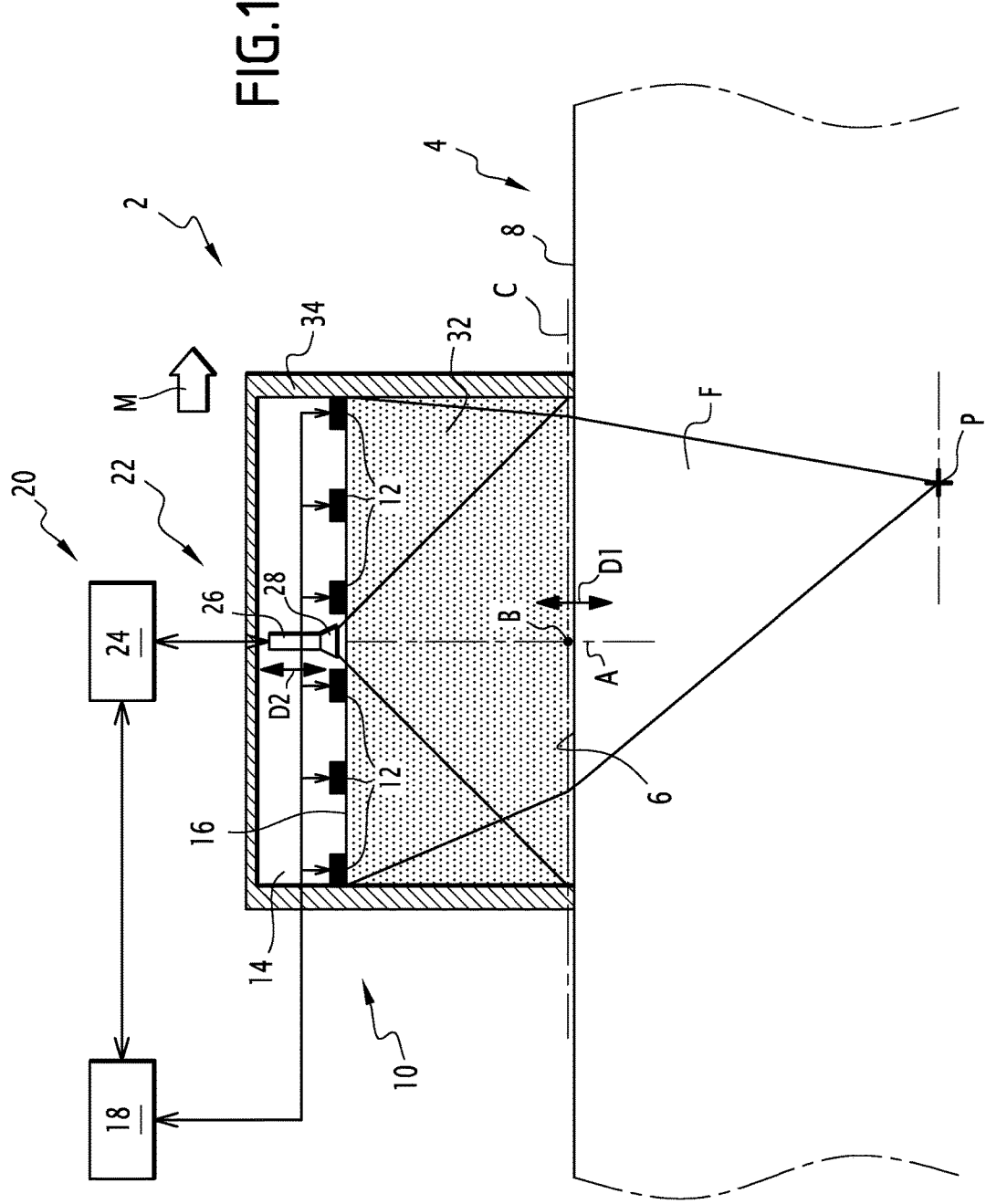
FIG. 1 is a schematic view of an ultrasonic probe for examining a part.

The ultrasonic probe 2 of FIG. 1 gives the possibility of proceeding with an examination of an object 4 by emitting a focused ultrasonic beam F inside the object 4 through an area 6 of a surface 8 of the object 4, and of receiving and analyzing the sound signals reflected by the object 4 in response to the emission of the focused ultrasonic beam F.

The area 6 of the surface 8 of the object 4 through which the focused ultrasonic beam F is sent inside the object 4 is called an « active area 6» hereafter.

The ultrasonic probe 2 comprises a transceiver device 10 able to emit a focused ultrasonic beam F and to receive a sound signal reflected by the object.

The transceiver device 10 comprises multiple emitter elements 12 each able to emit an elementary ultrasonic signal. The ultrasonic signals form together the focused ultrasonic beam F.

The emitter elements 12, or at least one portion of them, are also able to receive the reflected sound signals. These are transceiver elements.

Optionally or alternatively, the transceiver device 10 comprises receiver elements able to receive the reflected signals, which are distinct from the emitter elements 12.

The transceiver device 10 comprises a support of elements 14 having an emitting surface 16 on which are distributed the emitter elements 12. In the case of distinct receiver elements 12, these receiver elements are also distributed over the emitting surface.

The ultrasonic beam is the to be « focused » when it is directed towards a point of interest P of the object so as to concentrate the acoustic energy towards this point of interest P.

The ultrasonic signal emitted by each emitter element 12 has a travel time between the emitter element 12 and the targeted point of interest P.

In order to form a focused ultrasonic beam F towards a point of interest P, the ultrasonic elementary signals are emitted with time shifts so that they reach the point of interest in phase.

The ultrasonic probe 2 comprises an electronic processing module 18 able to control the transceiver device 4 for emitting a focused ultrasonic beam F.

The processing module 18 is programmed for determining a respective delay law for each emitter element 12, and for controlling the emission of ultrasonic signals by the emitter elements 12 depending on their respective delay laws.

Each delay law determines a time shift for emitting an elementary ultrasonic signal by the associated emitter element relatively to a reference signal.

The processing module 18 executes an algorithm for computing delay laws which determines for each emitter element 12 a respective delay law notably depending on the position of the point of interest P relatively to the ultrasonic probe 2.

The delay laws to be applied depend on the relief or profile of the active area 6 of the surface 8 of the object 4.

The ultrasonic probe 2 comprises an electronic profilometer 20 for determining the profile of the active area 6 located facing the emitting surface 16.

The profilometer 20 is capable of taking at least one digital image of the active area and of determining the profile of the active area 6 by analyzing the optical blurring on the or at least one digital image of the active area 6.

The profilometer 20 comprises an image-taking apparatus 22 for taking at least one digital image of the active area 6 and an electronic analysis module 24 able to determine the profile of the active area 6 by analyzing the optical blurring of the or at least one taken image.

The image-taking apparatus 22 is a digital apparatus for taking photographs or a digital camera. It conventionally comprises an optical photosensitive array sensor 26 for example a CCD or CMOS sensor.

The image-taking apparatus 22 comprises an optical objective 28. The optical sensor 26 is positioned for taking images through the optical objective 28. The optical objective 28 conventionally comprises one or several optical lenses.

The image-taking apparatus 22 has a field of vision which is the portion of the visible space on an image picture taken by the optical apparatus. The optical objective 28 is the first element of the image-taking apparatus 22 receiving the light from the field of vision of the image-taking apparatus 22.

When the ultrasonic probe 2 is applied against the surface 8 of the object 4, the image-taking apparatus 22 takes an image of the area 6 of the surface 8 of the object 4 located in the field of vision.

The optical objective 28 has an optical axis A, a focal point B at a distance from the optical objective 28 along the optical axis, and a focal plane C perpendicular to the optical axis A and passing through the focal point B.

An element found in the focal plane C will appear sharp on an image taken by the image-taking apparatus 22. Elements found in front or behind the focal plane C will appear blurred on an image taken by the image-taking apparatus 22. The farther away an element is from the focal plane C, the more it will appear blurred on the image.

The focal plane C is close to the surface 8 when the ultrasonic probe 2 is applied against the surface 8.

The analysis module 24 is able to process at least one image of the active area 6 by analyzing the optical blurring on the or at least one image so as to determine the profile of the active area.

The analysis module 24 is programmed so as to execute an algorithm for analyzing optical blurring. The algorithm for analyzing optical blurring for example is in a known way based on the analysis of the contrast in the image. Indeed, a digital image is formed by a matrix of pixels. The more a region of the digital image is blurred on a digital image, the lower is the contrast between the neighboring pixels of this region, and the sharper is a region of the digital image, the higher is the contrast between the neighboring pixels of this region. By analyzing the contrast gradients or by an equivalent analysis on the digital image of a surface, it is therefore possible to determine the profile of the surface.

In order to improve accuracy, it is possible to take several digital images of the active area 6 by varying the position of the focal plane C relatively to the active area 6 between the takings of images, and then to compare the images with each other and according to the variation of the position of the focal plane C.

To do this, in an embodiment, the optical objective 28 is an adjustable optical objective so as to move the focal plane C along with the optical axis A (arrow D1).

Preferably, the optical objective 28 is motor-driven and comprises a motor able to modify the adjustment, for example by moving one or several lenses of the optical objective 28.

Alternatively or optionally, the image-taking apparatus 22 in its entirety (optical sensor 26 and optical objective 28) is movable (arrow D2), for example by means of a displacement motor, so as to modify the distance, taken along the optical axis A, between the image-taking apparatus 22 and the active area 6 and to move the focal plane C relatively to the active area 6.

Alternatively or optionally, the emitting surface 16, the emitter elements 12 and the image-taking apparatus 22 are movable together, for example by means of a displacement motor, so as to modify the distance, taken along the optical axis A, between the image-taking apparatus 22 and the active area 6.

The processing module 18 is able to process the reflected signals received by the transceiver device 4. The processing module 18 is configured for determining the position, the shape and the dimensions of possible defects inside the examined object 4. Alternatively, the processing module 18 is configured so as to transmit the received signals to a remote electronic processing unit.

The ultrasonic probe 2 comprises a sound coupling device 32 configured so as to be interposed between the transceiver device 10 and the active area 6, so that the ultrasonic signals are emitted in the coupling device 32 and transmitted by the latter to the active area 6.

The sound coupling device 32 is provided for ensuring material continuity between the emitting surface 16 and the active area 6 for better transmission of sound waves. The sound coupling device 32 is provided so as to be in contact with the emitting surface and applied in contact against the active area 6.

The sound coupling device 32 is for example a rigid shoe in plastic material. Alternatively, the coupling device is a deformable cushion filled with a fluid, for example water, having a supporting surface intended to be applied against the surface of the part and able to conform with the surface of the object. This allows improved sound coupling as compared with a rigid shoe.

The image-taking apparatus 22 takes images of the active area 6 through the sound coupling device 32. For this purpose, the latter is transparent.

The ultrasonic probe 2 comprises a probe body 34 which may be moved along the surface 8 of the object 4. The element support 14 is attached on the probe body 34 so that the emitting surface 16 is facing the active area 6. The sound coupling device 32 is attached on the probe body 34 so as to be interposed between the emitting surface 16 and the active area 6. The image-taking apparatus 22 is attached on the probe body 34.

In the case when the image-taking apparatus 22 is movable for adjusting the position of the focal plane, the image-taking apparatus 22 is slidably mounted on the probe body 34 so as to slide along the optical axis A (arrow D2 in FIG. 1).

As illustrated in FIG. 1, the image-taking apparatus 22 is positioned so as to take an image of the active area 6 through the emitting surface 16, between the emitter elements 12 of the transceiver device 4.

Figure 2:
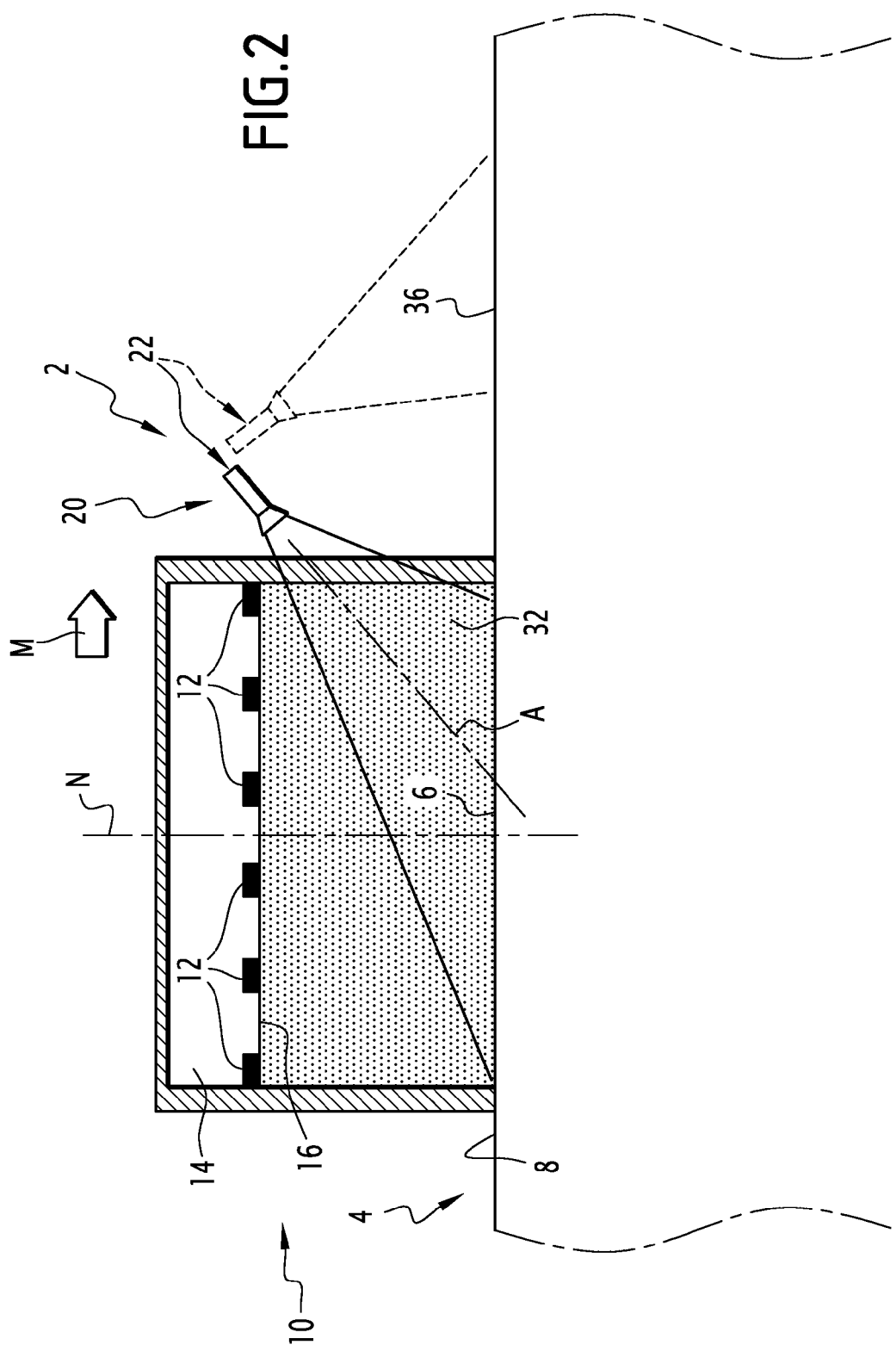
FIG. 2 is a schematic view of an ultrasonic probe according to an alternative.

Alternatively, as illustrated in FIG. 2, the image-taking apparatus 22 is positioned so that it is shifted relatively to the emitting surface 16 and that the emitting surface 16 is located outside the field of vision of the image-taking apparatus 22.

The image-taking apparatus 22 is tilted here so that its optical axis A forms a non-zero angle with the normal N to the active area 6. The image processing module comprises an image correction module known per se allowing this tilt to be taken into account.

In another alternative illustrated in dotted lines in FIG. 2, the image-taking apparatus is attached on the probe body so as to take an image of a downstream area 36 of the surface of the part shifted relatively to the active area 6 and located in front of the active area 6 on the trajectory of the ultrasonic probe 2 along the surface 8 of the object 4, by considering the displacement direction of the probe along the surface 8 (arrow M). With this layout, it is possible to determine the profile of an area in advance in order to then apply the determined delay laws when this area becomes the active area.

During operation, the ultrasonic probe 2 is applied against the active area 6 of the surface 8 of the object 4 to be examined.

Figure 3:
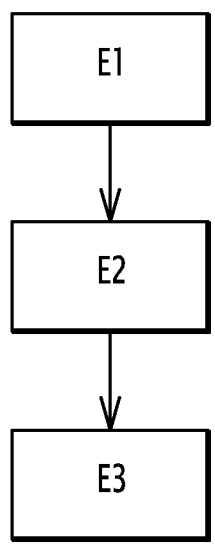
FIG. 3 is a diagram illustrating steps of a method for ultrasonic examination of a part.

As illustrated in FIG. 3, in a first step E1, the profilometer 20 determines the profile of the active area of the part. To do this, the image-taking apparatus 22 takes at least one digital image of the active area 6. The analysis module 24 determines the profile of the active area 6 by analyzing the optical blurring of the or at least one digital image of the active area 6 and transmits the determined profile to the processing module 18.

In a second step E2, the processing module 18 determines delay laws for the emitter elements 12 of the transceiver device 10. The control module 18 sends command instructions to the emitter elements 6, the instructions taking into account the delay laws for emitting an ultrasonic beam focused towards a point of interest of the examined object. The transceiver device 4 emits the focused ultrasonic beam F and it receives the sound signals reflected by the object in response to the focused ultrasonic beam F.

In a third step E3, the processing module 18 processes the received reflected sound signals so as to allow determination of the position, the shape and the dimensions of possible defects inside the examined object.

These steps are repeated in a cyclic way by moving the ultrasonic probe along the surface 8 (arrow M in FIGS. 1 and 2) in order to extensively examine the object 4 under an extent of the surface 8.

The profilometer by analysis of the optical blurring is simple and robust. It has a limited number of mechanical parts in motion. This limits maintenance and repair. This also limits the risk of losing parts, in particular in a nuclear reactor circuit, in which tiny debris may cause significant damages when they are carried away at great speed through the nuclear fuel assemblies. The device for profilometry with optical blurring allows determination of the profile of a surface with good resolution, which allows more accurate and more reliable examination by ultrasound. It is possible to obtain a resolution of the order of a tenth of a millimeter.

The ultrasonic probe may in particular be used for examining walls of the components of a nuclear reactor, as a non-limiting example, for examining underwater the wall of the nuclear reactor core. For such an examination, the probe is positioned at the end of a maneuvering rod which is maneuvered by an operator for moving the ultrasonic probe along the wall.

What is claimed is:

1. An ultrasonic probe for examining an object with ultrasound, the probe comprising:
   a plurality of emitter elements configured to emit ultrasonic waves for emitting a focused ultrasonic beam into the object through an active area of a surface of the object;
   a profilometer configured for determining the profile of the surface of the object and for controlling the emission of the ultrasonic beam depending on the determined profile, the profilometer including an image-taking apparatus configured for taking at least one digital image of the active area and an image processing module able to determine the profile of the active area by analyzing an optical blurring of the at least one image.

2. The ultrasonic probe as recited in claim 1 wherein the profilometer is configured for taking several images of the active area by moving a focal plane of the image-taking apparatus relative to the active area between the taking of images.

3. The ultrasonic probe as recited in claim 2 wherein the image-taking apparatus is movably mounted on a body of the ultrasonic probe so as to be configured for moving the focal plane of the image-taking apparatus relative to the active area between the taking of images.

4. The ultrasonic probe as recited in claim 2 wherein the image-taking apparatus has an optical objective which is adjustable so as to be configured for moving the focal plane of the image-taking apparatus relative to the active area between the taking of images.

5. The ultrasonic probe as recited in claim 1 wherein the image-taking apparatus is positioned so as to take images of the active area through an emitting surface on which the emitter elements are distributed, when the ultrasonic probe is applied against the object to be examined.

6. The ultrasonic probe as recited in claim 1 configured so that one emitting surface of the probe on which the emitter elements are distributed is outside a field of vision of the image-taking apparatus, when the probe is applied against the object to be examined.

7. The ultrasonic probe as recited in claim 6 wherein the ultrasonic probe is configured so that the image-taking apparatus takes images of the active area with a non-zero angle between an optical axis of the image-taking apparatus and a normal to the active area, when the probe is applied against the object to be examined.

8. The ultrasonic probe as recited in claim 1 wherein the image-taking apparatus is positioned so as to take images of an upstream area of the surface of the object located upstream from the active area during displacement of the probe along the surface of the object.

9. A method for non-destructive examination of an object having a surface, the method comprising:
   determining a profile of an active area of the surface by taking at least one digital image of the active area and analyzing the optical blurring of said at least one image by a profilometer; and
   emitting a focused ultrasonic beam into the object through the active area by a plurality of ultrasonic wave emitter elements, each ultrasonic wave emitter element being controlled depending on the determined profile.

10. The method as recited in claim 9 wherein several images of the active area are taken by an image-taking apparatus of the profilometer by modifying a relative position of the active area and of a focal plane of the image-taking apparatus between each taking of an image.

* * * * *